(12) United States Patent
Larson et al.

(10) Patent No.: US 9,101,305 B2
(45) Date of Patent: Aug. 11, 2015

(54) GLUCOSE SENSOR PRODUCT AND RELATED MANUFACTURING AND PACKAGING METHODS

(75) Inventors: Eric Allan Larson, Simi Valley, CA (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1190 days.

(21) Appl. No.: 13/044,367

(22) Filed: Mar. 9, 2011

(65) Prior Publication Data

US 2012/0227358 A1 Sep. 13, 2012

(51) Int. Cl.
*B65B 55/02* (2006.01)
*A61B 5/145* (2006.01)
*A61B 5/1486* (2006.01)

(52) U.S. Cl.
CPC ........... *A61B 5/14532* (2013.01); *A61B 5/1486* (2013.01); *A61B 2562/12* (2013.01); *A61B 2562/242* (2013.01)

(58) Field of Classification Search
CPC ...... B65B 55/02; B65B 55/027; B65B 55/10; B65B 55/103; B65B 55/022; B65B 55/06
See application file for complete search history.

(56) References Cited

U.S. PATENT DOCUMENTS

| | | | |
|---|---|---|---|
| 3,631,847 A | | 1/1972 | Hobbs, II |
| 3,991,881 A | * | 11/1976 | Augurt ........................... 206/439 |
| 4,091,921 A | * | 5/1978 | Lewis ............................ 206/363 |
| 4,121,714 A | * | 10/1978 | Daly et al. .................... 206/363 |
| 4,206,844 A | * | 6/1980 | Thukamoto et al. .......... 206/439 |
| 4,212,738 A | | 7/1980 | Henne |
| 4,270,532 A | | 6/1981 | Franetzki et al. |
| 4,282,872 A | | 8/1981 | Franetzki et al. |
| 4,373,527 A | | 2/1983 | Fischell |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

Dupont, DuPont Medical Packaging Technical Reference Guide, 2009.

(Continued)

*Primary Examiner* — Sameh Tawfik
(74) *Attorney, Agent, or Firm* — Ingrassia Fisher & Lorenz, P.C.

(57) ABSTRACT

A glucose sensor product is manufactured by a process that maintains the sterility of the glucose sensor while allowing gaseous manufacturing by-products to be vented from the inside of the glucose sensor package. The method begins by placing a glucose sensor assembly into a plastic package tray having a sealing surface surrounding an opening. The method continues by covering the opening with a microbial barrier material such that the microbial barrier material overlies the sealing surface, forming a seal between the sealing surface and the microbial barrier material, resulting in a sealed package tray containing the glucose sensor assembly, and sterilizing the glucose sensor assembly inside the sealed package tray. The microbial barrier material maintains sterility of the glucose sensor assembly while allowing volatile by-products outgassed from the glucose sensor assembly and the plastic package tray to pass therethrough.

6 Claims, 7 Drawing Sheets

(56) References Cited

U.S. PATENT DOCUMENTS

| | | | |
|---|---|---|---|
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,344,017 A * | 9/1994 | Wittrock | 206/459.1 |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,497,772 A | 3/1996 | Schulman et al. | |
| 5,505,709 A | 4/1996 | Funderburk et al. | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,233,471 B1 * | 5/2001 | Berner et al. | 600/345 |
| 6,246,992 B1 | 6/2001 | Brown | |
| 6,259,937 B1 | 7/2001 | Schulman et al. | |
| 6,329,161 B1 | 12/2001 | Heller et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |

(56) References Cited

U.S. PATENT DOCUMENTS

| | | | |
|---|---|---|---|
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,468,033 B2 | 12/2008 | Van Antwerp et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2009/0299301 A1 | 12/2009 | Gottlieb et al. |
| 2012/0000804 A1* | 1/2012 | Barnes et al. ............... 206/363 |
| 2012/0006717 A1* | 1/2012 | Zambaux ................. 206/524.6 |
| 2012/0305426 A1* | 12/2012 | Valaie et al. ............... 206/363 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS

PCT Search Report (PCT/US02/03299), Oct. 31, 2002, Medtronic MiniMed, Inc.

(Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(Intensive Diabetes Management, 1995). Insulin Infusion Pump Therapy. pp. 66-78.

Disetronic My Choice™ D-TRON™ Insulin Pump Reference Manual. (no date).

Disetronic H-TRON® plus Quick Start Manual. (no date).

(56) References Cited

OTHER PUBLICATIONS

Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifi-

(56) References Cited

OTHER PUBLICATIONS cal Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

GLUCOSE SENSOR PRODUCT AND RELATED MANUFACTURING AND PACKAGING METHODS

TECHNICAL FIELD

Embodiments of the subject matter described herein relate generally to medical devices and related packaging techniques. More particularly, embodiments of the subject matter relate to a glucose sensor product and its associated manufacturing and packaging processes.

BACKGROUND

The prior art includes a wide variety of medical devices and components, related manufacturing techniques, and related packaging techniques. For example, sensors are generally known in the art for use in a variety of specialized applications. In this regard, thin film electrochemical sensors are used to test analyte levels in patients. More specifically, thin film sensors have been designed for use in obtaining an indication of blood glucose (BG) levels and monitoring BG levels in a diabetic patient, with the distal segment portion of the sensor positioned subcutaneously in direct contact with patient extracellular fluid. Such readings can be especially useful in adjusting a treatment regimen which typically includes regular administration of insulin to the patient.

A glucose sensor of the type described above may be packaged and sold as a product that includes certain features or components that allow the patient to position and subcutaneously implant the sensor. For example, thin film glucose sensors are often implanted subcutaneously/transcutaneously using an introducer tool, which may be packaged with the glucose sensor. The introducer contains a needle that is used to puncture the skin of a patient at the same time as the sensor is introduced. The needle is then withdrawn, leaving the sensor in the skin of the patient. The introducer, or insertion device, commonly including a needle, is used and then discarded after inserting the sensor at the sensor site.

In practice, glucose sensors are provided in sterile packages, bags, or containers that keep the sensors protected and sterile until they are ready for insertion. During manufacturing, a glucose sensor is inserted into the desired package, which usually forms an airtight seal around the glucose sensor to provide the desired amount of protection. Thereafter, the sealed package is subjected to a sterilization procedure. After sterilization, the sealed package is prepared for shipping, boxing, or the like.

BRIEF SUMMARY

An exemplary embodiment of a method of manufacturing a medical device package is presented here. The method involves the fabrication of a medical device assembly. In accordance with the method, the medical device assembly is placed into a package tray. The method continues by sealing the medical device assembly inside the package tray with a gas-permeable sealing material, and sterilizing the medical device assembly inside the sealed package tray. The sealing material maintains sterility of the medical device assembly while allowing volatile substances to vent from inside the sealed package tray to outside the sealed package tray.

Also provided is an exemplary embodiment of a glucose sensor product manufactured by a process that involves the steps of: placing a glucose sensor assembly into a plastic package tray having a sealing surface surrounding an opening; covering the opening with a microbial barrier material such that the microbial barrier material overlies the sealing surface; forming a seal between the sealing surface and the microbial barrier material, resulting in a sealed package tray containing the glucose sensor assembly; and sterilizing the glucose sensor assembly inside the sealed package tray. The microbial barrier material maintains sterility of the glucose sensor assembly while allowing volatile by-products outgassed from the glucose sensor assembly and the plastic package tray to pass therethrough.

An exemplary embodiment of a glucose sensor product is also provided. The glucose sensor product includes a plastic package tray and a glucose sensor assembly in the plastic package tray. The glucose sensor assembly includes an electrochemical sensor with glucose oxidase enzyme, a sensor base formed at least in part from plastic, a sensor mounting pedestal formed at least in part from plastic, and a sensor introducer formed at least in part from plastic. The glucose sensor product also includes a microbial barrier material coupled to the plastic package tray to seal the glucose sensor assembly in the plastic package tray. The microbial barrier material maintains sterility of the glucose sensor assembly while venting substances outgassed from the plastic package tray, the sensor base, the sensor mounting pedestal, and the sensor introducer.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
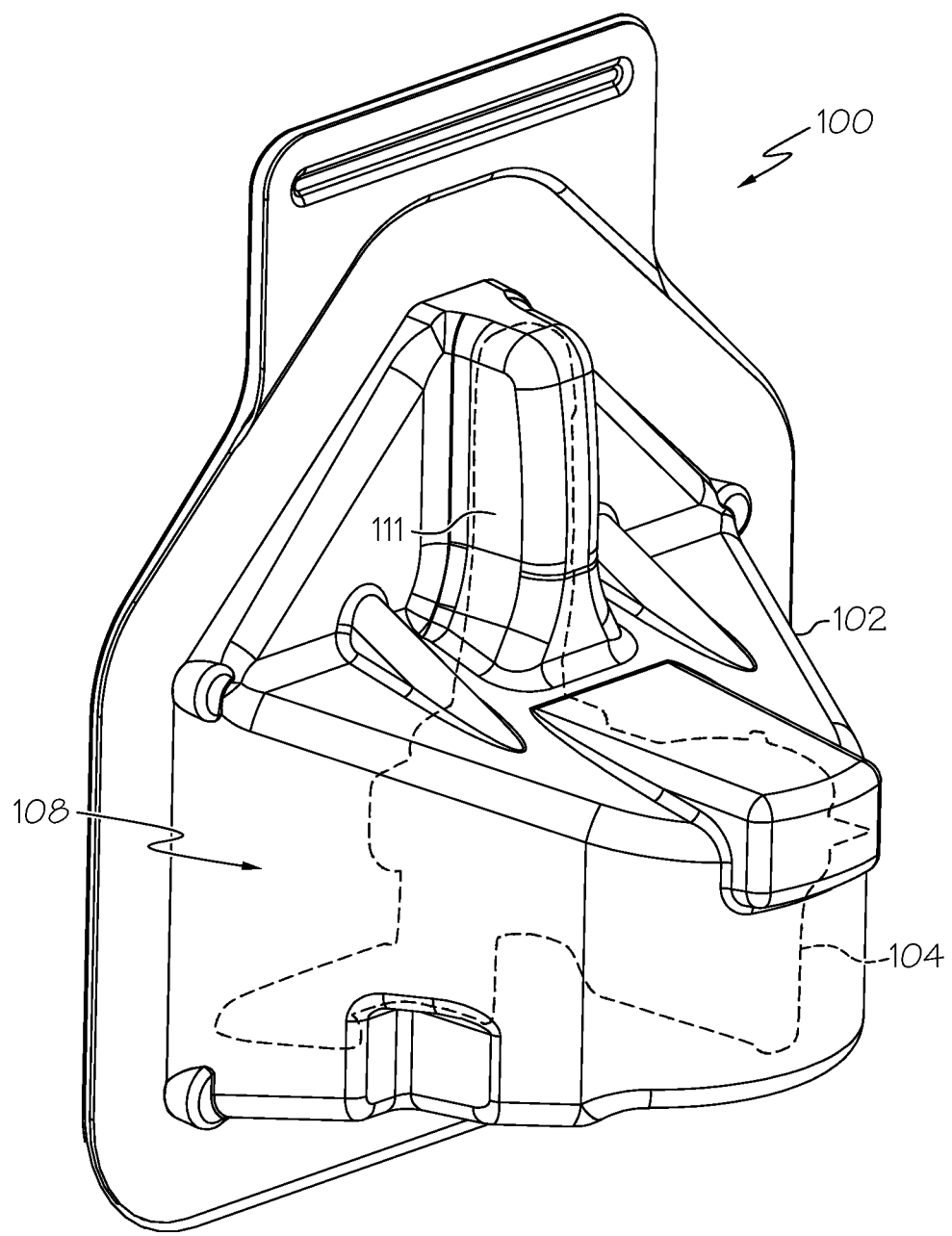
FIG. 1 is a rear perspective view of an exemplary embodiment of a glucose sensor package.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter described here relates to the manufacturing and packaging of a medical device or a medical component. The non-limiting exemplary embodiment described below relates to a continuous glucose sensor of the type used by diabetic patients. It should be appreciated that the manufacturing and packaging techniques presented here need not be limited to use with glucose sensors and, indeed, the concepts and technology described with reference to a glucose sensor could also be used with other medical devices, other sensor types, other medical components or supplies, and the like.

For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085 and 7,468,033, and United States patent application number 2009/0299301 (which are incorporated by reference herein).

A glucose sensor of the type described here may be realized as an electrochemical sensor that employs the glucose oxidase enzyme. Sensors that use glucose oxidase to effect a reaction of glucose and oxygen are known, and such glucose sensors will not be described in detail here. Sealed bagging represents one conventional approach for packaging glucose sensors that use the glucose oxidase enzyme. In accordance with this packaging technique, an assembled glucose sensor product is sealed inside of a plastic bag, and the sealed bag is thereafter subjected to a sterilization process. The sealed plastic bag serves as a barrier to microbes and other contaminants. The non-permeable nature of the plastic bag, however, keeps solvents, outgassed substances, and/or other by-products of the manufacturing and sterilization processes trapped inside the plastic bag. For example, plastics, adhesives, and packaging materials may release (outgas) chemicals, solvents, or gases during and after manufacturing, and after the glucose sensor product has been sealed inside the plastic bag. Some trapped substances and gases may have little to no effect on the glucose sensor (more specifically, the glucose oxidase enzyme), while other trapped substances and gases may be volatile in that they might degrade or otherwise interact with the glucose oxidase enzyme in an undesirable manner.

Experiments and empirical data indicate that glucose sensors in sealed plastic bags tend to drift after they have been deployed. In other words, the generated output voltage/current for a given glucose level trends in an escalating manner over time. In addition, sensor signals may also drift downward (loss of signal) over time due to depletion of available enzyme or physical blockage from bodily debris (lipids, biofilm, immune response) or otherwise, while drifting upward can be a result of other instabilities in chemistry processing such as delamination or erosion of the various layers. It is feasible that there are complex interactions not fully understood that can cause drift either upward or downward as a result of sensor packaging and the subsequent interaction of the chemical layers with solvents. To compensate for such drifting, such glucose sensors may need to be calibrated and checked frequently. The hypothesis is that certain substances and gases trapped inside the sealed plastic bags adversely affect the quality and accuracy of the glucose sensors by interacting with the glucose oxidase enzyme. This suggests that a glucose sensor sealed in a plastic bag for a relatively short period of time before use might be more stable than a glucose sensor sealed in a plastic bag for a relatively long period of time before use. The manufacturing and packaging techniques presented here reduce the drift in output observed for glucose sensors in sealed packages.

Figure 2:
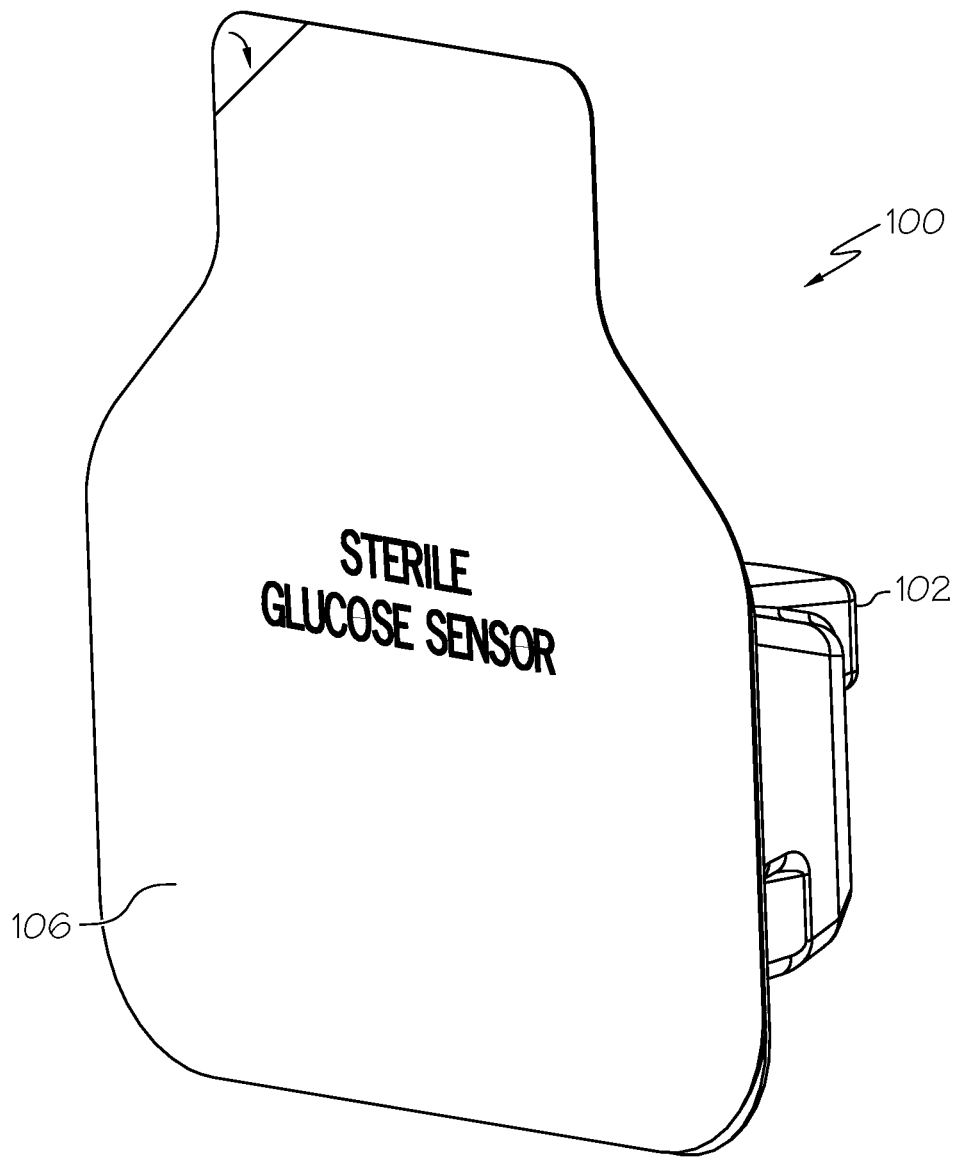
FIG. 2 is a front perspective view of the glucose sensor package shown in FIG. 1.
Figure 3:
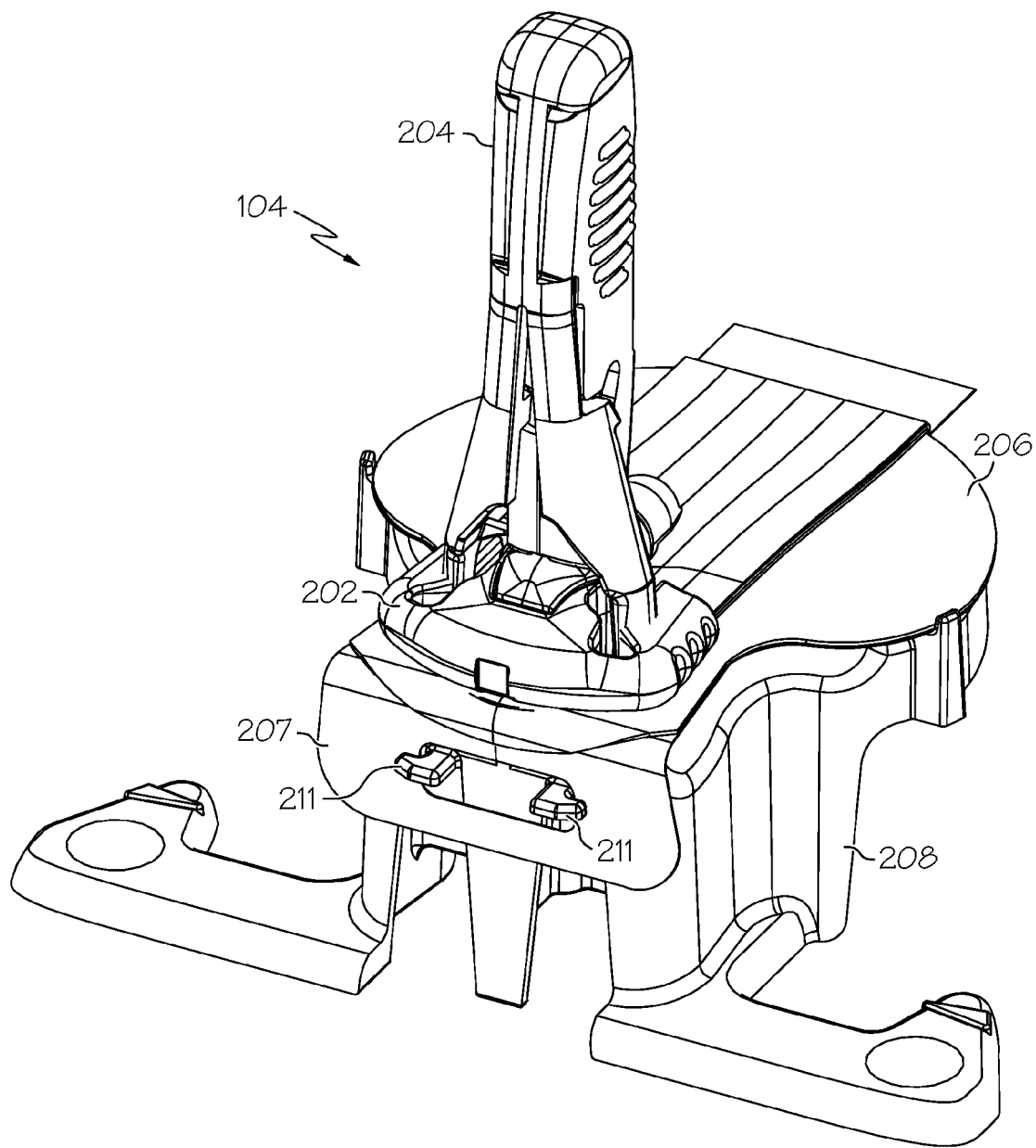
FIG. 3 is a perspective view of the glucose sensor assembly contained in the glucose sensor package shown in FIG. 1.

FIG. 1 is a rear perspective view of an exemplary embodiment of a glucose sensor package 100, and FIG. 2 is a front perspective view of the glucose sensor package 100. The glucose sensor package 100 represents one exemplary form factor that can be used for purposes of boxing, shipping, storing, and distributing glucose sensors that have been manufactured, assembled, and sterilized in accordance with the techniques and processes described here. This particular embodiment of the glucose sensor package 100 generally includes, without limitation: a package tray 102; a glucose sensor assembly 104 (shown in phantom); and a piece of material 106. FIG. 3 is a perspective view of the glucose sensor assembly 104, FIG. 4 is an exploded perspective view of the glucose sensor assembly 104, and FIG. 5 is a front perspective view of the package tray 102.

In certain embodiments the package tray 102 is composed at least in part from a plastic material. For the embodiment described here, the package tray 102 is formed as a one-piece molded plastic component. The package tray 102 is formed as a solid component that is free of holes, tears, punctures, etc. In practice, the package tray 102 may be formed from a thermoformed or injection molded plastic material such as, without limitation: polypropylene, polycarbonate (PC), acrylonitrile butadiene styrene (ABS), a PC/ABS blend, nylon, polyvinyl chloride (PVC), and preferably formed from a polyethylene terephthalate glycol (PETG) material. The package tray 102 can be formed from a transparent or clear plastic material such that the glucose sensor assembly 104 is visible.

The glucose sensor assembly 104 resides in an interior cavity 108 of the package tray 102; the interior cavity 108 may be shaped and sized in a manner that generally conforms to the glucose sensor assembly 104. In this regard, the package tray 102 may include a retaining feature 111 (also shown in FIG. 1) that accommodates a component of the glucose sensor assembly 104. The purpose of this retaining feature 111 is described in more detail below. Referring to FIG. 5, the front of the package tray 102 includes an opening 110 that leads to the interior cavity 108. The front of the package tray 102 also includes a sealing surface 112, which surrounds the opening 110. For ease of illustration, the sealing surface 112 is shaded in FIG. 5. Referring also to FIG. 2, the material 106 covers the opening 110 and is coupled to the package tray 102 in a manner that forms a seal between the sealing surface 112 and the material 106. In other words, the material 106 serves as a cover that encloses the glucose sensor assembly 104 within the interior cavity 108.

Figure 4:
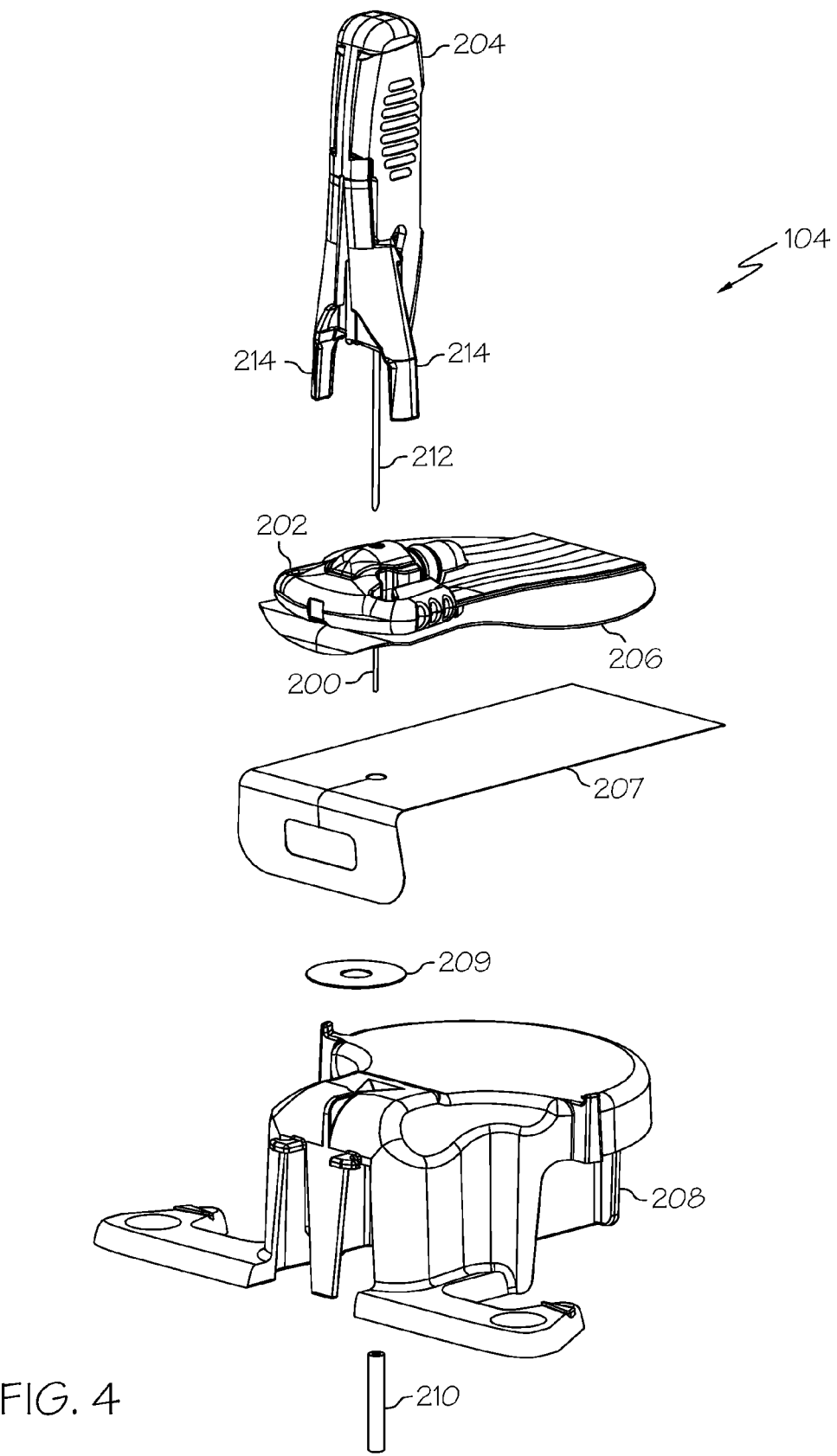
FIG. 4 is an exploded perspective view of the glucose sensor assembly shown in FIG. 3.
Figure 5:
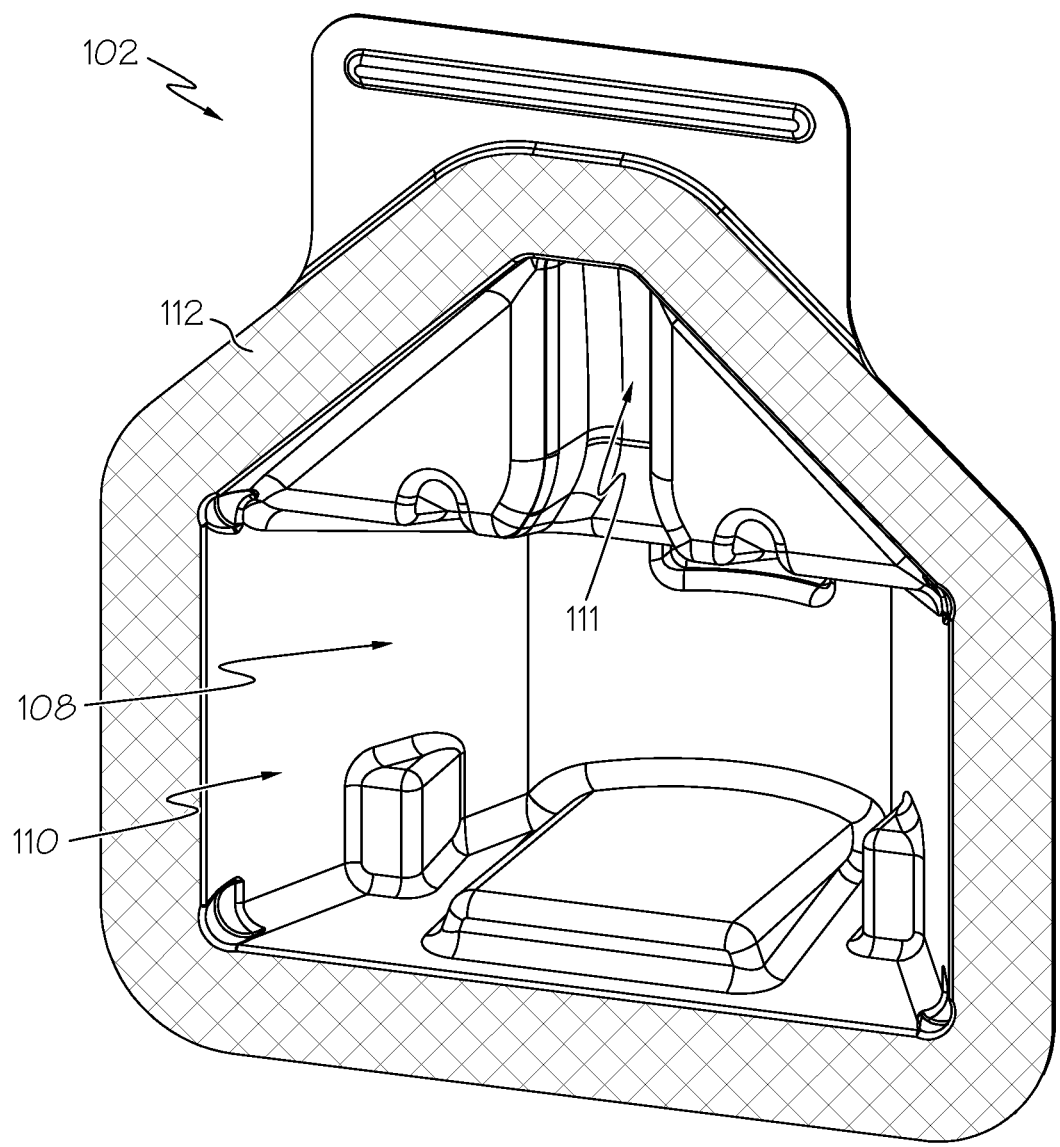
FIG. 5 is a front perspective view of the package tray shown in FIG. 1.

Referring now to FIG. 3 and FIG. 4, the illustrated embodiment of the glucose sensor assembly 104 generally includes, without limitation: a glucose sensor 200; a sensor base 202 coupled to the glucose sensor 200; a sensor introducer 204 that cooperates with the sensor base 202; a mounting base 206 for the sensor base 202; a liner 207; a sensor mounting pedestal 208; and an adhesive disk 209. The glucose sensor assembly 104 may also include a needle guard 210, which is an optional element that can be used with certain embodiments. As depicted in FIG. 1 and FIG. 3, the components of the glucose sensor assembly 104 are coupled together as a single unit for placement in the package tray 102. Many features, aspects, and characteristics of the glucose sensor assembly 104 and its individual elements are conventional and, as such, will not be described in detail here.

The glucose sensor 200 may be realized as an electrochemical sensor that includes the glucose oxidase enzyme, as is well understood by those familiar with glucose sensor technology. The glucose oxidase enzyme enables the glucose sensor 200 to monitor blood glucose levels in a diabetic patient by effecting a reaction of glucose and oxygen. Again, although certain embodiments pertain to glucose sensors, the manufacturing and packaging technology described here can be adapted for use with any one of the wide variety of sensors known in the art.

The glucose sensor 200 may be provided as an integral part of the sensor base 202, as depicted in FIG. 4. The sensor base 202 gives structural support to the glucose sensor 200, and facilitates entry of the glucose sensor 200 into the body of the patient. The sensor base 202 may also feature electrical and physical interfaces and elements that accommodate an electronics module (not shown), such as a wireless transmitter that communicates with an infusion pump, a monitor device, or the like. In certain embodiments the sensor base 202 is composed at least in part from a plastic material. For the embodiment described here, the bulk of the sensor base 202 is formed as a molded plastic component. In practice, the sensor base 202 may be formed from ABS, nylon, an ABS/PC blend, PVC, polytetrafluoroethylene (PTFE), polypropylene, polyether ether ketone (PEEK), or the like, and preferably polycarbonate.

The sensor introducer 204 is manipulated to introduce the glucose sensor 200 into the body of the patient. The sensor introducer 204 includes a spring loaded needle 212 and mating components 214 that engage corresponding features on the sensor base 202. FIG. 4 depicts the needle 212 in its extended position, where the needle 212 protrudes from the body of the sensor introducer 204. The sensor introducer 204 connects to the sensor base 202 before introducing the glucose sensor 200 into the body of the patient. The sensor introducer 204 and the sensor base 202 can be pre-connected as part of a sensor set, which could also include a sensor electronics module that connects to the sensor base 202 after insertion of the glucose sensor 200 in the body of the patient. Alternatively, the sensor introducer 204, the sensor base 202, and the glucose sensor 200 could be packaged and provided together, as depicted in FIG. 3. In certain embodiments the sensor introducer 204 is composed at least in part from a plastic material. For the embodiment described here, the bulk of the sensor introducer 204 is formed as a molded plastic component. In practice, the sensor introducer 204 may be formed from any of the materials mentioned above for the sensor base 202, and is preferably formed from polycarbonate.

The mounting base 206 affixes the sensor base 202 to the skin of the patient. The mounting base 206 may be made out of a flexible and breathable material with adhesive properties, such as cloth, a bandage-like material, and the like. For example, suitable materials could include polyurethane, polyethylene, polyester, polypropylene, polytetrafluoroethylene (PTFE), or other polymers. The top side of the mounting base 206 is adapted to be attached to the sensor base 202 (and to the sensor electronics module, which is not shown). The bottom side of the mounting base 206 is adapted to be attached to the skin of the patient using an adhesive. An additional adhesive layer and the liner 207 may also be provided on the bottom of the mounting base 206 to temporarily secure the mounting base 206 to the sensor mounting pedestal 208 during packaging, shipping, and handling. In this regard, the adhesive disk 209 may be a double-sided adhesive element that maintains the liner 207 in position atop the sensor mounting pedestal 208. In turn, the mounting base 206 is maintained in position due to adhesion to the upper surface of the liner 207.

Figure 6:
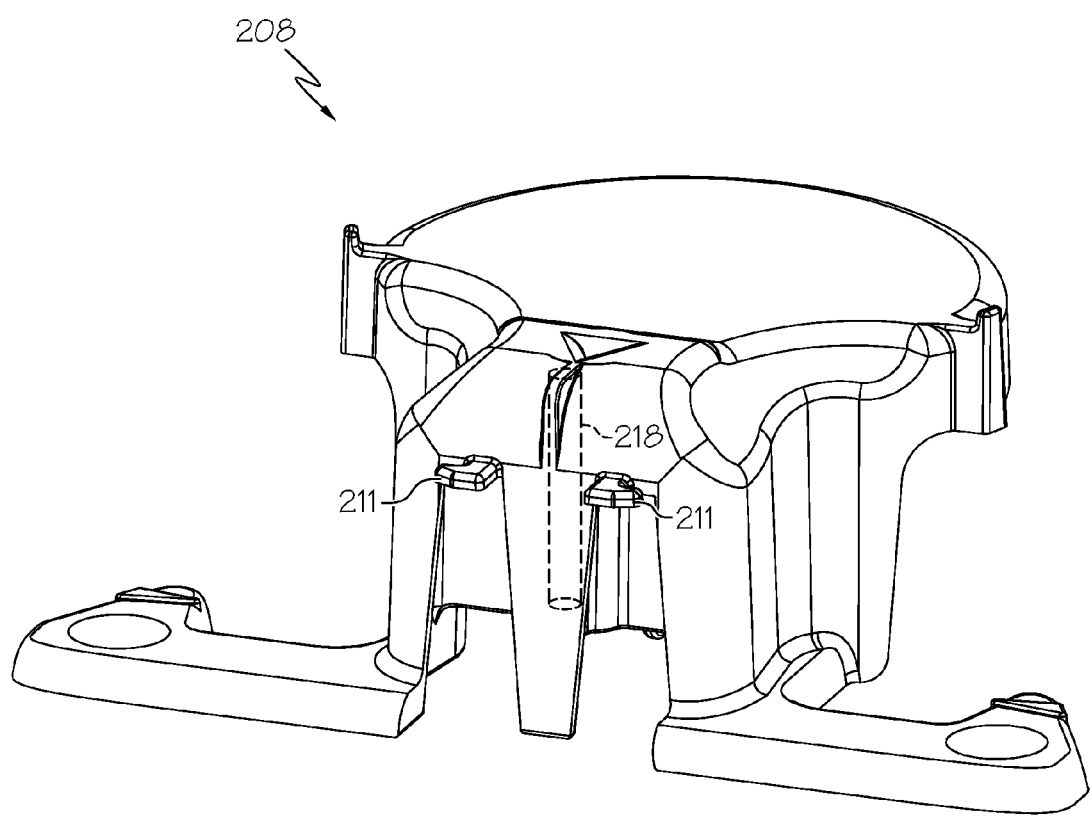
FIG. 6 is a perspective view of a sensor mounting pedestal suitable for use with the glucose sensor assembly shown in FIG. 3.

Referring also to FIG. 6, the sensor mounting pedestal 208 includes a needle sleeve 218 formed therein, which receives and protects the needle 212 and the glucose sensor 200 during packaging, shipping, and handling. The optional needle guard 210 resides within the needle sleeve 218, and it is composed of a soft and pliable material (such as silicone) for added protection of the needle 212. The sensor mounting pedestal 208 provides a sturdy protective platform for the glucose sensor assembly 104, as illustrated in FIG. 3. Thus, the glucose sensor assembly 104 can be placed into the package tray 102 as an integral unit. Referring again to FIG. 1 and FIG. 5, the sensor introducer 204 fits within the retaining feature 111 such that the needle 212 is protected during shipping and handling. The conformal nature of the package tray 102 ensures that the sensor introducer 204 and, therefore, the needle 212, remains in place relative to the sensor mounting pedestal 208 until the user removes the glucose sensor assembly 104 from the package.

As shown in FIG. 3 and FIG. 6, this particular embodiment of the sensor mounting pedestal 208 includes a liner holder 211 that engages an edge, a hole, tabs, or any cooperating feature of the liner 207. In the illustrated implementation, the liner holder 211 is realized as two projecting "hooks" that extend from the front of the sensor mounting pedestal 208. As shown in FIG. 3, the liner holder 211 engages and holds the liner 207 when the glucose sensor assembly 104 is assembled. The liner holder 211 "catches" the liner 207 when the user separates the sensor mounting pedestal 208 from the rest of the assembly. More specifically, the liner holder 211 retains the liner 207 when the sensor mounting pedestal 208 and the adhesive element of the mounting base 206 are separated. This separation action may be accomplished via manual or automated insertion methodologies. The separation action results in the removal of the liner 207 from the bottom of the mounting base 206, which exposes some of the adhesive surface of the mounting base 206. The separation action also exposes the needle 212 such that it can be inserted into the skin. The liner holder 211 simplifies the insertion procedure and eliminates the need for the user to manually remove the liner 207 from the mounting base 206.

In certain embodiments the sensor mounting pedestal 208 is composed at least in part from a plastic material. For the embodiment described here, the bulk of the sensor mounting pedestal 208 is formed as a molded plastic component. In practice, the sensor mounting pedestal 208 may be formed from any of the materials mentioned above for the sensor base 202, and is preferably formed from polypropylene.

The material 106 forms a seal around the package tray 102, but it accommodates venting from inside the package tray 102 to outside the glucose sensor package 100. In this regard, the material 106 may be considered to be gas-permeable (at least in the inside-out direction) such that it allows volatile substances to vent from inside the sealed package tray 102 to outside the sealed package tray 102. In particular, the composition of the material 106 is such that it vents volatile substances that would otherwise degrade the glucose oxidase enzyme of the glucose sensor 200. Moreover, the material 106 has certain properties and characteristics that allow it to vent substances outgassed or otherwise produced from the materials used to fabricate the glucose sensor assembly 104. For example, certain chemicals, solvents, and/or gases may be produced from the plastic materials used to form the package tray 102, the sensor base 202, the sensor introducer 204, the mounting base 206, the adhesives, and the sensor mounting pedestal 208. Substances outgassed from these components and/or used during the fabrication of these components may include, without limitation: alcohol; ethanol; solvents; volatile (non)condensable materials; low-molecular-weight additives; reactive diluents; absorbed moisture; and the like. The material 106 allows these substances to exit the sealed package tray 102 such that they do not significantly degrade or otherwise adversely interact with the glucose oxidase enzyme of the glucose sensor 200.

The material 106 also serves as a microbial barrier that seals and protects the glucose sensor assembly 104 inside the package tray 102. As described in more detail below, the sealed package tray 102 is sterilized and the material 106 maintains the sterile condition of the glucose sensor assembly 104 while allowing the volatile manufacturing by-products to pass therethrough. Thus, the microbial barrier material 106 allows unwanted chemicals and substances to exit the glucose sensor package 100 while preventing contaminants from entering the sealed package tray 102 and otherwise maintaining the sterility of the glucose sensor assembly 104. The composition of the material 106 may include, for example, a high-density polyethylene, polyester, or polypropylene. In certain embodiments, the material 106 may be composed of TYVEK material, which is available from DuPont.

The glucose sensor assembly 104 can be removed from the package tray 102 by peeling away the material 106. Thereafter, the sensor mounting pedestal 208 is removed and the adhesive bottom surface of the mounting base 206 is exposed so that it can be adhered to the skin of the patient. The needle 212 of the sensor introducer 204 is used to penetrate the skin of the patient, such that the glucose sensor 200 enters the body of the patient. In this regard, the needle 212 is extended when the sensor base 202 is connected to the sensor introducer 204, and the glucose sensor 200 resides within the needle 212. The user inserts the needle 212 into the body of the patient, which introduces the glucose sensor 200 under the skin. After introducing the glucose sensor 200 in this manner, the user disconnects the sensor introducer 204 from the sensor base 202, leaving the sensor base 202 and the glucose sensor 200 in place.

Figure 7:
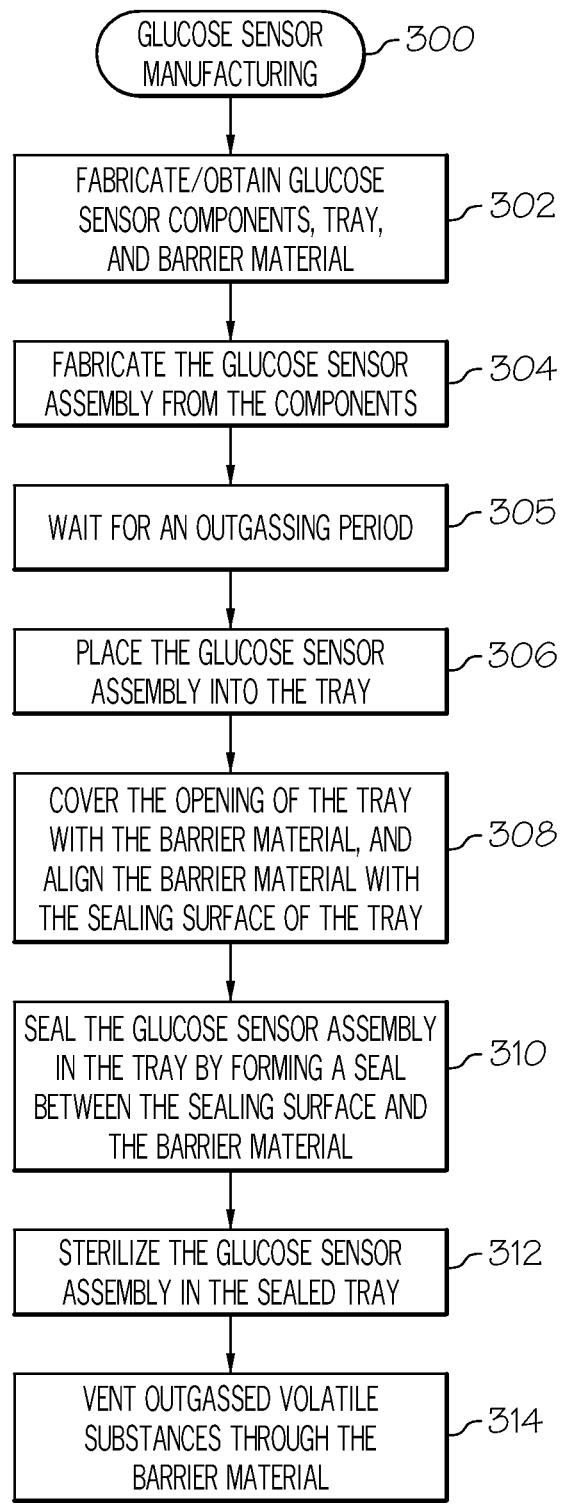
FIG. 7 is a flow chart that illustrates an exemplary embodiment of a glucose sensor manufacturing process.

FIG. 7 is a flow chart that illustrates an exemplary embodiment of a glucose sensor manufacturing process 300, which may be carried out to fabricate a glucose sensor product such as the glucose sensor package 100. It should be appreciated that the process 300 may include any number of additional or alternative tasks, the tasks shown in FIG. 7 need not be performed in the illustrated order, and the process 300 may be incorporated into a more comprehensive procedure or process having additional functionality not described in detail herein. Moreover, one or more of the tasks shown in FIG. 7 could be omitted from an embodiment of the process 300 as long as the intended overall functionality remains intact.

The manufacturing process 300 may begin by fabricating or otherwise obtaining the various glucose sensor components, the package tray, and the barrier/sealing material (task 302). The glucose sensor components can then be fabricated into the glucose sensor assembly (see FIG. 3) and prepared for packaging (task 304). After the glucose sensor assembly has been fabricated, it may be stored in an open air environment for a designated period of time to accommodate outgassing of substances from the glucose sensor assembly (task 305). For example, the glucose sensor assembly may be placed in a well ventilated area for the desired amount of time before proceeding with the manufacturing process 300.

After the outgassing period has lapsed, the glucose sensor assembly is placed and positioned inside the package tray (task 306), and the opening of the package tray is covered with the barrier/sealing material (task 308). As depicted in FIG. 2, the barrier/sealing material is positioned and aligned with the sealing surface of the package tray prior to sealing. In this regard, some of the barrier/sealing material overlies the sealing surface of the package tray. Next, the glucose sensor assembly is sealed inside the package tray with the barrier/sealing material (task 310). In practice, a seal is formed between the sealing surface of the package tray and the barrier/sealing material, resulting in a sealed package tray containing the glucose sensor assembly. This seal can be formed by applying heat and pressing the barrier/sealing material against the sealing surface of the package tray.

The sealed package tray can then be subjected to a sterilization procedure to sterilize the glucose sensor assembly inside the sealed package tray (task 312). The glucose sensor assembly may be sterilized by radiating the sealed package tray with sterilizing energy. In practice, electron beam sterilization or any suitable radiation sterilization technique may be employed during task 312 to sterilize the glucose sensor assembly. Notably, the barrier/sealing material maintains the sterility of the glucose sensor assembly while also allowing volatile substances (gases, chemicals, solvents, or the like) to vent and escape from inside the sealed package tray to the outside environment (task 314). As mentioned above, the barrier/sealing material may be a gas-permeable membrane that allows certain manufacturing by-products (which may be outgassed from the plastic and other materials that form the glucose sensor assembly) to pass through without compromising the sterile conditions inside the sealed package tray.

The sterilized glucose sensor package can then be labeled, stored, shipped, displayed, and otherwise handled for distribution and sale. The barrier/sealing material allows potentially volatile substances to vent rather than collect inside the sealed package tray. As described above, the venting of such volatiles is desirable to preserve the integrity and stability of the glucose sensor, and to extend the shelf life of the glucose sensor product.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of manufacturing a medical device package, the method comprising:
fabricating a medical device assembly;
placing the medical device assembly into a package tray;
sealing the medical device assembly inside the package tray with a gas-permeable sealing material, resulting in a sealed package tray; and
sterilizing the medical device assembly inside the sealed package tray, wherein the sealing material maintains sterility of the medical device assembly while allowing volatile substances to vent from inside the sealed package tray to outside the sealed package tray wherein the medical device assembly comprises an electrochemical sensor with glucose oxidase enzyme; and the sealing material vents volatile substances that would otherwise degrade the glucose oxidase enzyme.

2. The method of claim 1, wherein:
the medical device assembly comprises a sensor mounting pedestal for the electrochemical sensor, the sensor mounting pedestal formed at least in part from a plastic material; and the sealing material vents volatile substances outgassed from the plastic material.

3. The method of claim 1, wherein:

the medical device assembly comprises a sensor introducer for the electrochemical sensor, the sensor introducer formed at least in part from a plastic material; and the sealing material vents volatile substances outgassed from the plastic material.

4. The method of claim 1, wherein the package tray is formed at least in part from a plastic material; and the sealing material vents volatile substances outgassed from the plastic material.

5. The method of claim 1, wherein the sealing material is composed of high-density polyethylene that forms a microbial barrier for the medical device assembly.

6. The method of claim 1, wherein sterilizing the medical device assembly comprises radiating the sealed package tray with sterilizing energy.

\* \* \* \* \*